(12) United States Patent
Sharps

(10) Patent No.: US 9,351,770 B2
(45) Date of Patent: May 31, 2016

(54) SYSTEM AND METHOD FOR SPINAL DEFORMITY CORRECTION

(71) Applicant: Chester H. Sharps, Manakin Sabot, VA (US)

(72) Inventor: Chester H. Sharps, Manakin Sabot, VA (US)

(*) Notice: Subject to any disclaimer, the term of this patent is extended or adjusted under 35 U.S.C. 154(b) by 163 days.

(21) Appl. No.: 14/253,322

(22) Filed: Apr. 15, 2014

(65) Prior Publication Data

US 2015/0080963 A1    Mar. 19, 2015

Related U.S. Application Data

(60) Provisional application No. 61/877,321, filed on Sep. 13, 2013.

(51) Int. Cl.
*A61B 17/70*    (2006.01)
*A61B 17/88*    (2006.01)

(52) U.S. Cl.
CPC ........... *A61B 17/708* (2013.01); *A61B 17/7032* (2013.01); *A61B 17/8875* (2013.01)

(58) Field of Classification Search
CPC .......................... A61B 17/7032; A61B 17/708
See application file for complete search history.

(56) References Cited

U.S. PATENT DOCUMENTS

| 6,235,028 | B1* | 5/2001 | Brumfield | A61B 17/7083 |
| | | | | 606/53 |
| 8,382,811 | B2* | 2/2013 | Crook | A61B 17/7037 |
| | | | | 411/412 |
| 8,512,382 | B2* | 8/2013 | Cawley | A61B 17/7035 |
| | | | | 606/265 |
| 9,011,447 | B2* | 4/2015 | Arnett | A61B 17/7002 |
| | | | | 606/279 |
| 2007/0213715 | A1* | 9/2007 | Bridwell | A61B 17/025 |
| | | | | 606/264 |
| 2007/0213716 | A1* | 9/2007 | Lenke | A61B 17/025 |
| | | | | 606/264 |
| 2013/0211453 | A1* | 8/2013 | Lenke | A61B 17/708 |
| | | | | 606/250 |
| 2013/0253596 | A1 | 9/2013 | Crook et al. | |
| 2013/0338717 | A1 | 12/2013 | Cawley et al. | |

* cited by examiner

*Primary Examiner* — Ellen C Hammond
(74) *Attorney, Agent, or Firm* — Clements Bernard PLLC; Christopher L. Bernard; Lawrence A. Baratta, Jr.

(57) ABSTRACT

A system and associated surgical method for the correction of a spinal deformity by derotating one or more vertebrae of the spine, including: a rotation rod; a cephalad extender configured to be rotatably coupled to the rotation rod and coupled to a cephalad vertebra; a caudal extender configured to be rotatably coupled to the rotation rod and coupled to a caudal vertebra; and one or more intermediate extenders configured to be coupled to one or more intermediate vertebrae; wherein, when the rotation rod is rotated, a portion of the rotation rod engages a portion of the one or more intermediate extenders, causing the one or more intermediate extenders to rotate about an axis of the spine, thereby causing the one or more intermediate vertebrae to also rotate about the axis. The extenders are each coupled to their respective vertebra via a pedicle screw or the like.

8 Claims, 15 Drawing Sheets

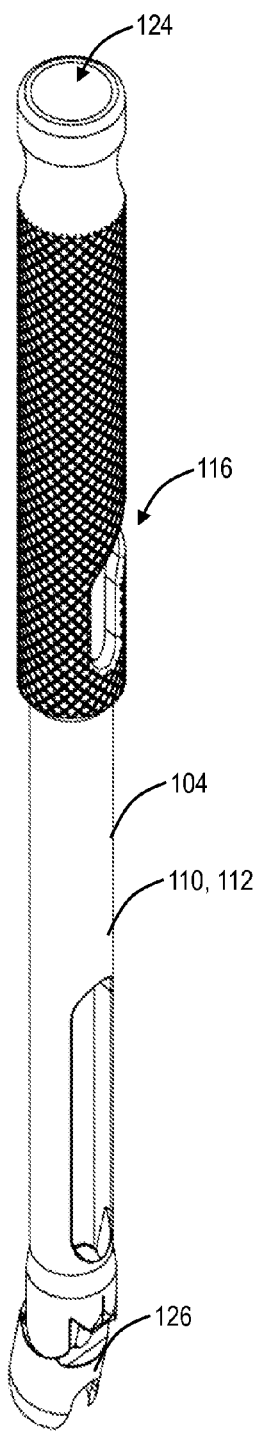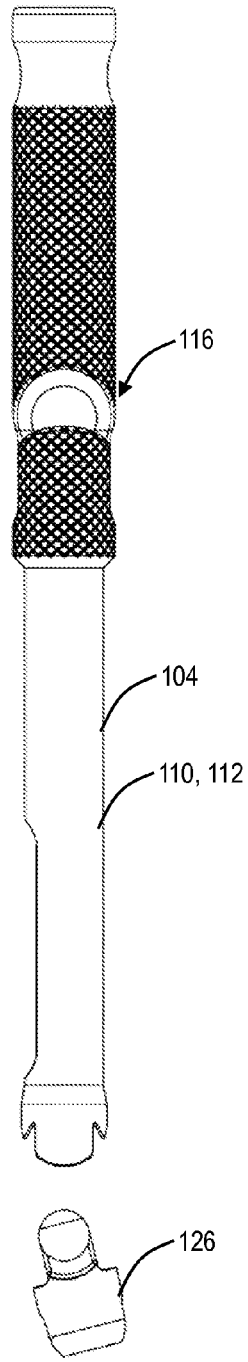
FIG. 7  FIG. 8

SYSTEM AND METHOD FOR SPINAL DEFORMITY CORRECTION

CROSS-REFERENCE TO RELATED APPLICATION

The present patent application/patent claims the benefit of priority of U.S. Provisional Patent Application No. 61/877,321, filed on Sep. 13, 2013, and entitled "SYSTEM AND METHOD FOR SPINAL DEFORMITY CORRECTION," the contents of which are incorporated in full by reference herein.

FIELD OF THE INVENTION

The present invention relates generally to the medical and spinal surgery fields. More specifically, the present invention relates to a system and method for spinal deformity correction.

BACKGROUND OF THE INVENTION

A number of conventional systems and methods exist for the correction of spinal deformities, such as scoliosis. In general, these systems and methods are used to "derotate" the spine when one or more vertebrae are rotated axially at an angle that is not aligned with the patient's sagittal plane. Once the spine is derotated (or simultaneous with derotation), pedicle screws and rods or the like are placed and secured to maintain derotation. Typically, conventional systems and methods have been ineffective, cumbersome, and difficult to use.

The spine may have a treatment region including cephalad vertebrae and caudal vertebrae. The cephalad vertebrae are located at the cephalad end of the treatment region (i.e. the end nearest the head of the patient). The caudal vertebrae are located at the caudal end of the treatment region (i.e. the end furthest from the head of the patient). There may also be one or more intermediate vertebrae disposed between the cephalad vertebrae and the caudal vertebrae. The cephalad vertebrae and the caudal vertebrae may be in proper sagittal alignment, while some or all of the intermediate vertebrae may be in need of derotation.

Thus, what is still needed in the art is a system and method for spinal deformity correction that is effective, simple, and easy to use, such that patients may be treated more successfully in shorter surgical times.

BRIEF SUMMARY OF THE INVENTION

In one exemplary embodiment, the present invention provides a system for the correction of a spinal deformity by derotating one or more vertebrae of the spine, including: a rotation rod; a cephalad extender configured to be selectively rotatably coupled to the rotation rod and coupled to a cephalad vertebra of the spine; a caudal extender configured to be selectively rotatably coupled to the rotation rod and coupled to a caudal vertebra of the spine; and one or more intermediate extenders configured to be selectively coupled to one or more intermediate vertebrae of the spine; wherein, when the rotation rod is selectively rotated, a portion of the rotation rod engages a portion of the one or more intermediate extenders, causing the one or more intermediate extenders to rotate about an axis of the spine, thereby causing the one or more intermediate vertebrae to rotate about the axis of the spine. The system also includes a rotation handle configured to be selectively coupled to the rotation rod. Optionally, the rotation rod includes an off-axis portion that engages the portion of the one or more intermediate extenders. Optionally, the rotation rod further includes a roller disposed about the off-axis portion that engages the portion of the one or more intermediate extenders. Preferably, the cephalad extender, the caudal extender, and the one or more intermediate extenders are each coupled to their respective vertebra via a pedicle screw. Optionally, one or more of the cephalad extender and the caudal extender include an end portion that is one or more or pivotable and rotatable (and lockable) and that selectively retains a head of the respective pedicle screw. One or more of the cephalad extender and the caudal extender include a locking mechanism for selectively preventing relative rotation with the rotation rod. Optionally, the system further includes a coupling mechanism for rotatably coupling the one or more intermediate extenders to the rotation rod. Finally, the system includes a rod system or the like configured to, via the pedicle screws, secure the spine in a derotated state after the one or more intermediate vertebrae are rotated about the axis of the spine.

In another exemplary embodiment, the present invention provides a method for the correction of a spinal deformity by derotating one or more vertebrae of the spine, including: coupling a cephalad extender to a cephalad vertebra of the spine; coupling a caudal extender to a caudal vertebra of the spine; coupling one or more intermediate extenders to one or more intermediate vertebrae of the spine; rotatably coupling a rotation rod to the cephalad extender and the caudal extender; and rotating the rotation rod; wherein, when the rotation rod is rotated, a portion of the rotation rod engages a portion of the one or more intermediate extenders, causing the one or more intermediate extenders to rotate about an axis of the spine, thereby causing the one or more intermediate vertebrae to rotate about the axis of the spine. The method also includes coupling a rotation handle to the rotation rod. Optionally, the rotation rod includes an off-axis portion that engages the portion of the one or more intermediate extenders. Optionally, the rotation rod further includes a roller disposed about the off-axis portion that engages the portion of the one or more intermediate extenders. Preferably, the cephalad extender, the caudal extender, and the one or more intermediate extenders are each coupled to their respective vertebra via a pedicle screw. Optionally, one or more of the cephalad extender and the caudal extender include an end portion that is one or more or pivotable and rotatable (and lockable) and that selectively retains a head of the respective pedicle screw. One or more of the cephalad extender and the caudal extender include a locking mechanism for selectively preventing relative rotation with the rotation rod. Optionally, the method further includes providing a coupling mechanism for rotatably coupling the one or more intermediate extenders to the rotation rod. Finally, the method includes providing a rod system or the like configured to, via the pedicle screws, secure the spine in a derotated state after the one or more intermediate vertebrae are rotated about the axis of the spine.

BRIEF DESCRIPTION OF THE DRAWINGS

The present invention is illustrated and described herein with reference to the various drawings, in which like reference numbers are used to denote like system components/methods steps, as appropriate, and in which:

FIG. 7 is a perspective view illustrating one exemplary embodiment of a cephalad/caudal extender of the spinal deformity correction system of FIG. 1;

FIG. 8 is a partially exploded planar side view further illustrating the cephalad/caudal extender of FIG. 7;

DETAILED DESCRIPTION OF THE INVENTION

Figure 1:
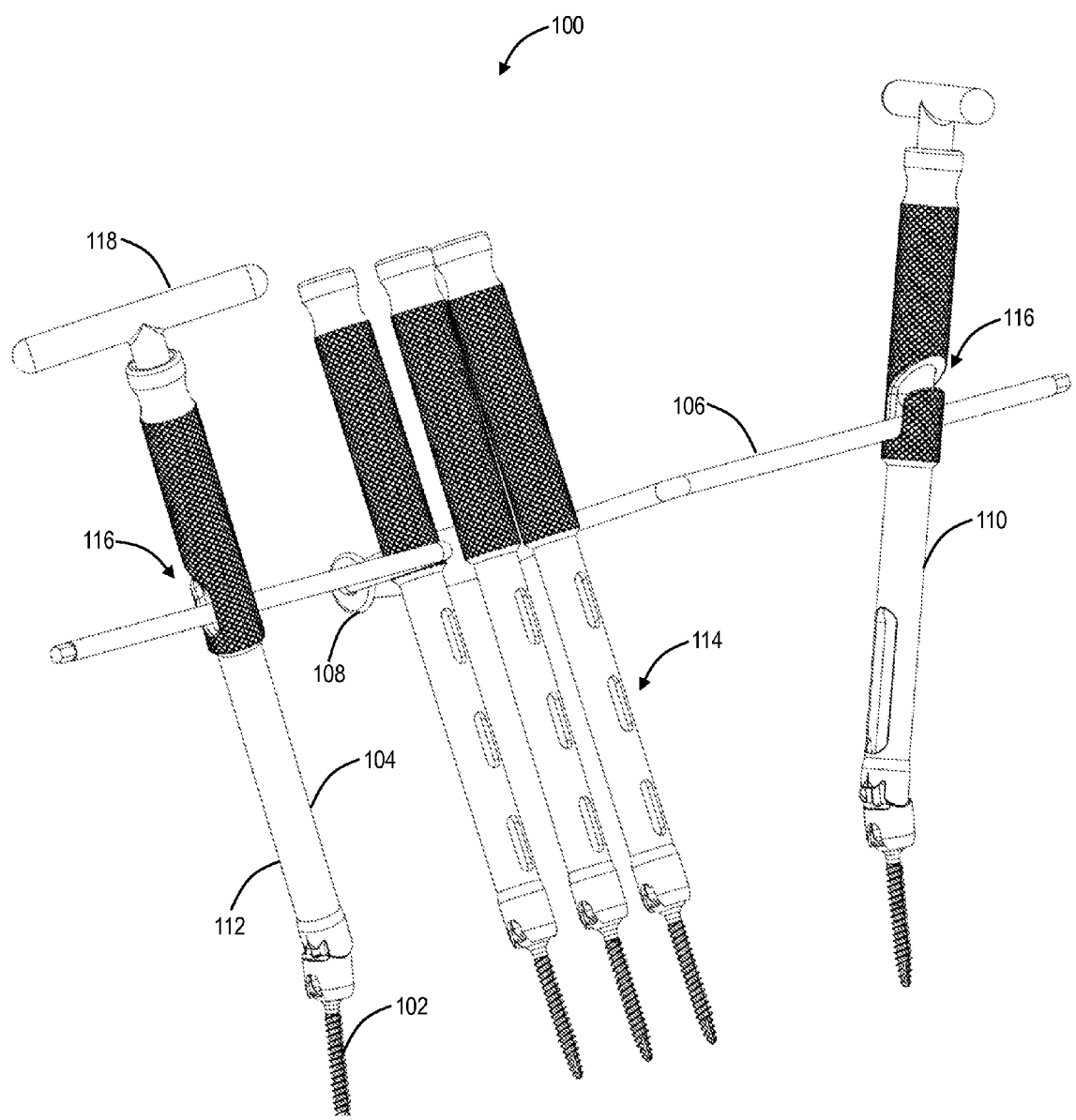
FIG. 1 is a perspective view illustrating one exemplary embodiment of the spinal deformity correction system of the present invention.

Referring now specifically to FIG. 1, in one exemplary embodiment, the spinal deformity correction system 100 of the present invention facilitates the correction of a spinal deformity, such as scoliosis, and may, more specifically, be used to derotate a spine in which one or more vertebrae are rotated axially at an angle that is not aligned with the patient's sagittal plane, i.e. the system 100 may be used to derotate vertebrae that are out of sagittal alignment. The spine may have a treatment region including a cephalad vertebra and a caudal vertebra. The cephalad vertebra is at the cephalad end of the treatment region (i.e. the end nearest the head of the patient) and the caudal vertebra is at the caudal end of the treatment region (i.e. the end furthest from the head of the patient). The spine also has one or more intermediate vertebrae disposed between the cephalad vertebra and the caudal vertebra. The cephalad vertebra and the caudal vertebra may be in proper sagittal alignment, while some or all of the intermediate vertebrae may be the vertebrae that are in need of derotation.

The system 100 is used in conjunction with an implantable pedicle screw and rod system or the like, well known to those of ordinary skill in the art, that is designed to securely maintain proper spacing and/or angulation between the vertebrae of the spine. Such a system may have pedicle screws or the like secured to one or both pedicles of each vertebra, and one or more connecting rods or the like, each of which is secured to multiple pedicle screws to provide the necessary long-term fixation. Such an implantable pedicle screw and rod system may be a rod contouring system, in which the connecting rods are custom contoured by the surgeon to provide the proper lordosis and/or kyphosis for the patient's spine. Thus, the system 100 may be used to provide derotation of the spine, and the implantable pedicle screw and rod system or the like may be used to keep the spine in this derotated state.

Other procedures well known to those of ordinary skill in the art may also be used to restore proper lordosis, kyphosis, and/or lateral straightness to the spine, in addition to the derotation provided by the system 100. Such procedures may be applied before, while, or after the system 100 is used, and may involve the use of the implantable pedicle screw and rod system, as set forth above, or a comparable system. For example, the implantable pedicle screw and rod system may be that disclosed in U.S. Patent Application Publication No. 2007/0233062 (now abandoned), assigned to Amedica Corp. of Salt Lake City, Utah, and entitled "Pedicle Screw System With Offset Stabilizer Rod," the contents of which are incorporated in full by reference herein.

Such an implantable pedicle screw and rod system may include pedicle screws, which may be secured to the vertebrae of the treatment region of the spine, for example, as part of a process for restoring lordosis, kyphosis, and/or lateral straightness, as set forth above. Additionally, the implantable pedicle screw and rod system may further include extenders, which may be secured to the pedicle screws and used to provide leverage for the process of restoring lordosis, kyphosis, and/or lateral straightness, as set forth above. Thus, the pedicle screws and/or the extenders may be any of a wide variety of pedicle screws and/or extenders known to those of ordinary skill in the art of spinal deformity correction.

Alternatively, the pedicle screws 102 and/or the extenders 104 may be provided as part of the system 100 and may be used only for the method carried out by the system 100 or in conjunction with the method carried out by the system. The system 100 also includes a rotation rod 106 and a rotation handle 108, which may be used in connection with the extenders 104 to carry out derotation. As illustrated in FIG. 1, the extenders 104 may include a cephalad extender 110 attachable to a pedicle screw 102 on the cephalad vertebra, a caudal extender 112 attachable to a pedicle screw 102 on the caudal vertebra, and one or more intermediate extenders 114 attachable to the pedicle screws 102 on the intermediate vertebrae. The system 100 may be applied unilaterally, with extenders 104 attached only to the pedicle screws 102 on one side of the spine. Alternatively, the system 100 may be applied bilaterally, with extenders 104 attached to the pedicle screws 102 on both sides of the spine. Each of the extenders 104 has a proximal end furthest from the associated pedicle screw 102, a distal end secured to the pedicle screw 102, and an intermediate portion between the proximal end and the distal end. If desired, the cephalad extender 110, the caudal extender 112, and the intermediate extenders 114 may all be identical to each other. Alternatively, the cephalad extender 110 and the caudal extender 112 may each have a feature not present on the intermediate extenders 114, such as a coupling mechanism 116 on or proximate the proximal end or the intermediate portion to receive the ends of the rotation rod 106, thereby rotatably securing the cephalad extender 110 and the caudal extender 112 to the rotation rod 106. This coupling mechanism 116 may or may not be present on the intermediate extenders 114.

Each coupling mechanism 116 takes the form of a notch or the like, again, rotatably securing the cephalad extender 110 and the caudal extender 112 to the rotation rod 106. Alternatively, the coupling mechanisms 116 may be positioned off-axis with respect to the cephalad extender 110 and the caudal extender 112, such that the ends of the rotation rod 106 pass alongside the cephalad extender 110 and the caudal extender 112. As illustrated, each coupling mechanism 116 may be positioned within an opening of the intermediate portion of the cephalad extender 110 and the caudal extender 112, such that its axis intersects that of the cephalad extender 110 and the caudal extender 112, allowing the rotation rod 106 to pass through the intermediate portion.

Figure 14:
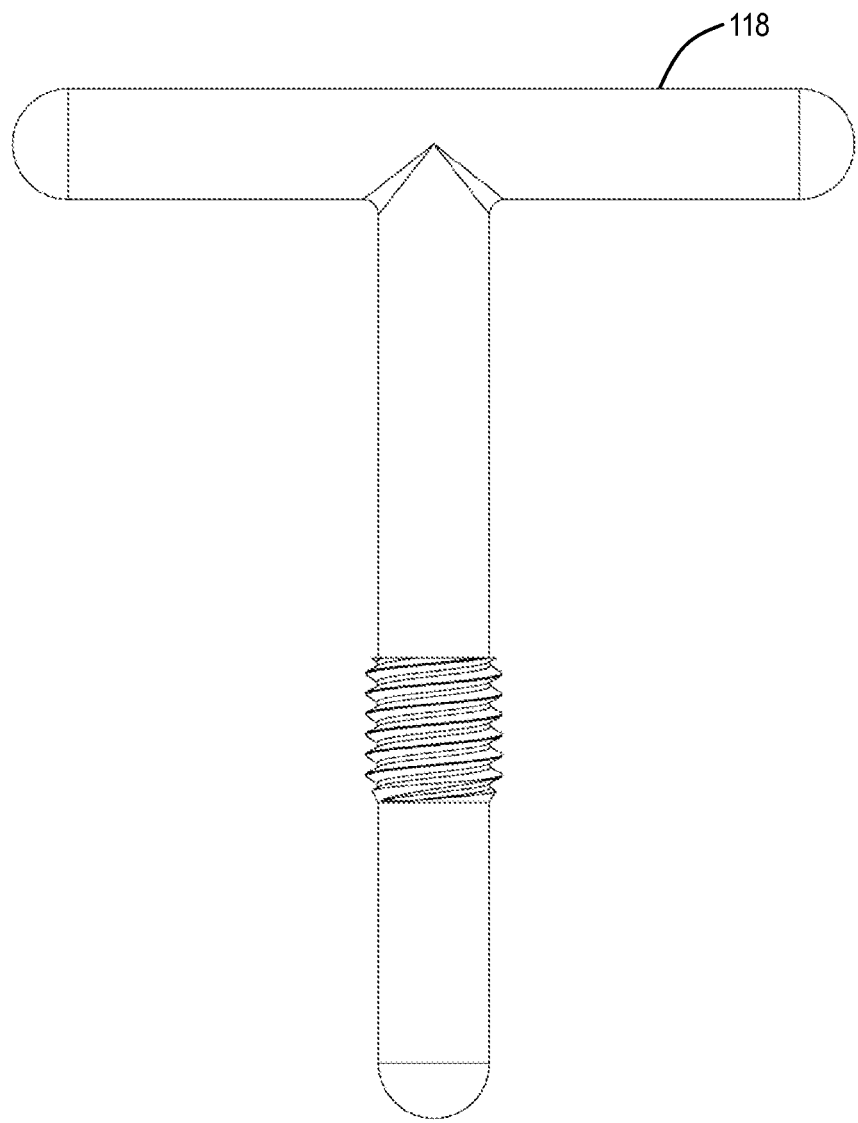
FIG. 14 is a planar side view illustrating one exemplary embodiment of a locking handle of the spinal deformity correction system of FIG. 1.

In one exemplary embodiment, the coupling mechanism 116 of the cephalad extender 110 and the coupling mechanism 116 of the caudal extender 112 may have a locking mechanism 118, such as a partially threaded rotatable handle (see FIG. 14) or the like, that may be actuated to restrict or prevent relative rotation between the rotation rod 106 and the cephalad extender 110 and/or the caudal extender 112. Such locking mechanism 118 may include any known structure for preventing relative rotation between two parts. Thus, the locking mechanism 118 may include a handle and set screw, collet, locking feature, or the like. In the alternative, an external device, such as a clamp, may be used. Such external device may be secured to an operating table or other fixed structure. As another alternative, such locking mechanism 118 may be omitted entirely, and the rotation rod 106 may simply be held in place by hand for the required duration.

In another exemplary embodiment (not illustrated), each extender 104 may have two distal ends, each of which is securable to one pedicle screw 102. The two distal ends may be coupled together via a bridge or the like. The two distal ends of each extender 104 may be secured to two pedicle screws 102 on a single vertebra. Such a bilateral design may provide for more secure attachment of each extender 104 to the corresponding vertebra, and may also help to transfer the forces induced on the vertebrae by the derotation process to a larger bone mass, thereby reducing any risk of damage to the vertebrae of the spine.

Figure 15:
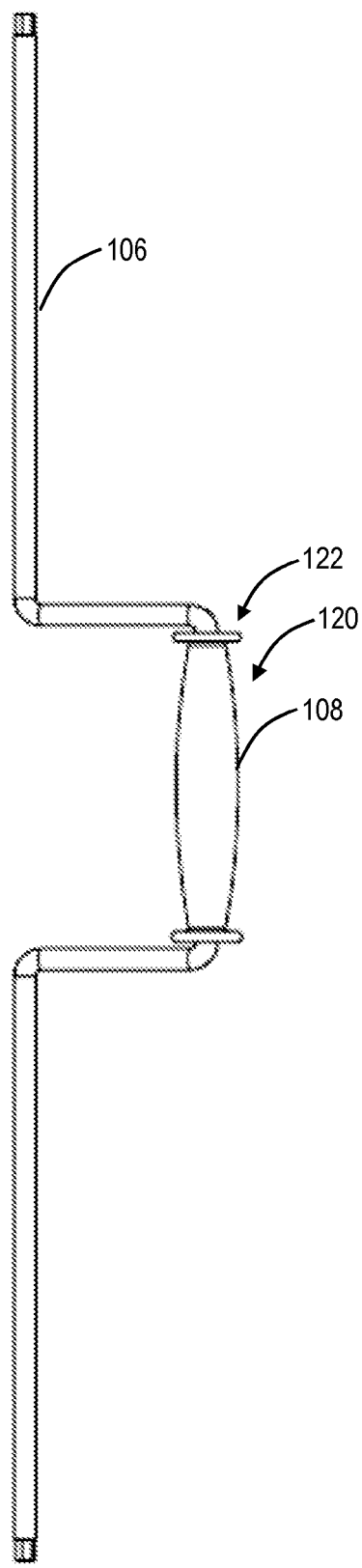
FIG. 15 is a planar side view illustrating one exemplary embodiment of a rotation rod of the spinal deformity correction system of FIG. 1.

Referring now specifically to FIG. 15, the rotation rod 106 may have a cephalad end positioned proximate the cephalad vertebra, a caudal end positioned proximate the caudal vertebra, and an intermediate portion that extends from the cephalad end to the caudal end, spanning the intermediate vertebrae. The cephalad end and the caudal end of the rotation rod 106 may generally be coaxial with each other. However, the rotation rod 106 may have nonlinear shape. The intermediate portion may have an off-axis bend by which the intermediate portion is displaced from the axis of the cephalad end and the caudal end, and on which the handle 108 is disposed. This off-axis bend may include a set of 90° bends between straight segments that provide the crankshaft-like shape of the intermediate portion shown in FIG. 15, which may provide the off-axis bend with a relatively uniform displacement along its length from the axis of the cephalad end and the caudal end. In alternative exemplary embodiments, the off-axis bend may be curved, angled, or otherwise shaped to provide a variable displacement from the axis of the cephalad and caudal ends of the rotation rod 106.

The intermediate vertebrae may initially be rotated (i.e. by a deformity of the patient's spine, such as scoliosis) such that the posterior elements of the intermediate vertebrae are shifted leftward, for example. Thus, the proximal ends of the intermediate extenders 114 may extend further leftward than the proximal ends of the cephalad extender 110 and the caudal extender 112. The off-axis bend allows the rotation rod 106 to rotate to push the proximal ends of the intermediate extenders 114 to the right, for example, such that the proximal ends of the intermediate extenders 114 align with those of the cephalad extender 110 and the caudal extender 112, or are even pushed rightward of the proximal ends of the cephalad extender 110 and the caudal extender 112. This rightward rotation of the proximal ends helps to correct the deformity, and, in particular, the component of the deformity that relates to improper axial rotation of the intermediate vertebrae.

Referring again specifically to FIG. 15, the rotation rod 106 may have a handle or roller 108 that is rotatably coupled to the intermediate portion thereof so that, as the rotation rod 106 rotates, the roller 108 may remain in contact with and exert lateral force against the intermediate extenders 114. The roller 108 may have a shaped surface 120 and two flanges 122 positioned at the cephalad and caudal ends of the roller 108. The shaped surface 120 may be cylindrical in shape, so as to keep the intermediate extenders 114 generally aligned with each other, or may have a different shape, such as the bulged shape shown in FIG. 15. The bulged shape may cause the proximal end of the centermost intermediate extender 114 to be pushed further rightward than the proximal ends of the surrounding intermediate extenders 114. Thus, the centermost intermediate extender 114 may receive more derotation (i.e. corrective rotation) than the surrounding intermediate extenders 114. In alternative exemplary embodiments, the shaped surface 120 may be shaped in any desired manner, for example, a cylinder, as set forth above, or an hourglass shape that causes the centermost intermediate extender 114 to receive less derotation than that of the surrounding intermediate extenders 114. The shape of the surface 120 may thus be custom tailored to the specific derotation needs of the intermediate vertebrae 104.

The flanges 122 help to keep the proximal ends of the intermediate extenders 114 in an abutting relationship with the surface 120. More precisely, the flanges 122 keep the proximal ends from sliding off of the roller 108 in the cephalad or caudal directions.

Optionally, an external rotation handle (not illustrated) having a proximal end and a distal end is selectively or fixedly coupled to the rotation rod 106. The proximal end may be securable to the rotation rod 106 so that the distal end may be gripped, for example, by hand, and rotated to induce rotation of the rotation rod 106. The rotation handle may be sufficiently long to provide the leverage needed for the surgeon to manually derotate the intermediate vertebrae 104. The proximal end of the rotation handle may be secured to the rotation rod 106 at any desired location, such as at the cephalad end, the caudal end, or the intermediate portion. The proximal end of the rotation handle may have an attachment interface designed to prevent relative rotation, such as wrench flats or the like. The portion of the rotation rod 106 that receives the rotation handle (i.e. the cephalad end or the caudal end) may have corresponding features, such as a polygonal interface that mates with the attachment interface in a manner that prevents relative rotation between the rotation rod 106 and the rotation handle. If desired, the proximal end of the rotation handle may have an opening that receives the corresponding portion of the rotation rod 106; the opening may not be fully encircled so as to permit entry of the rotation rod 106 into the opening from a direction nonparallel to the axis of the opening. According to one exemplary embodiment, the rotation handle may be a wrench of a type well known to those of ordinary skill in the art, with a hexagonal opening, and the corresponding features of the rotation rod 106 may be hexagonal flats received by the wrench. The wrench may have an adjustable opening to permit relatively easy attachment to and detachment from the hexagonal flats.

Once the rotation handle has been secured to the rotation rod 106, the rotation handle may be rotated, for example, by grasping the distal end of the rotation handle by hand and pushing or pulling it. The coupling mechanisms of the cephalad extender 110 and the caudal extender 112 retain the cephalad end and the caudal end, respectively, of the rotation rod 106 while permitting rotation of the rotation rod 106. This rotation of the rotation rod 106 causes the roller 108 to press against the proximal ends of the intermediate extenders 114, causing the proximal ends to shift rightward or leftward. This causes the intermediate vertebrae to rotate counterclockwise or clockwise, when viewed from a cranial viewpoint, relative to the cephalad vertebra and the caudal vertebra.

Figure 2:
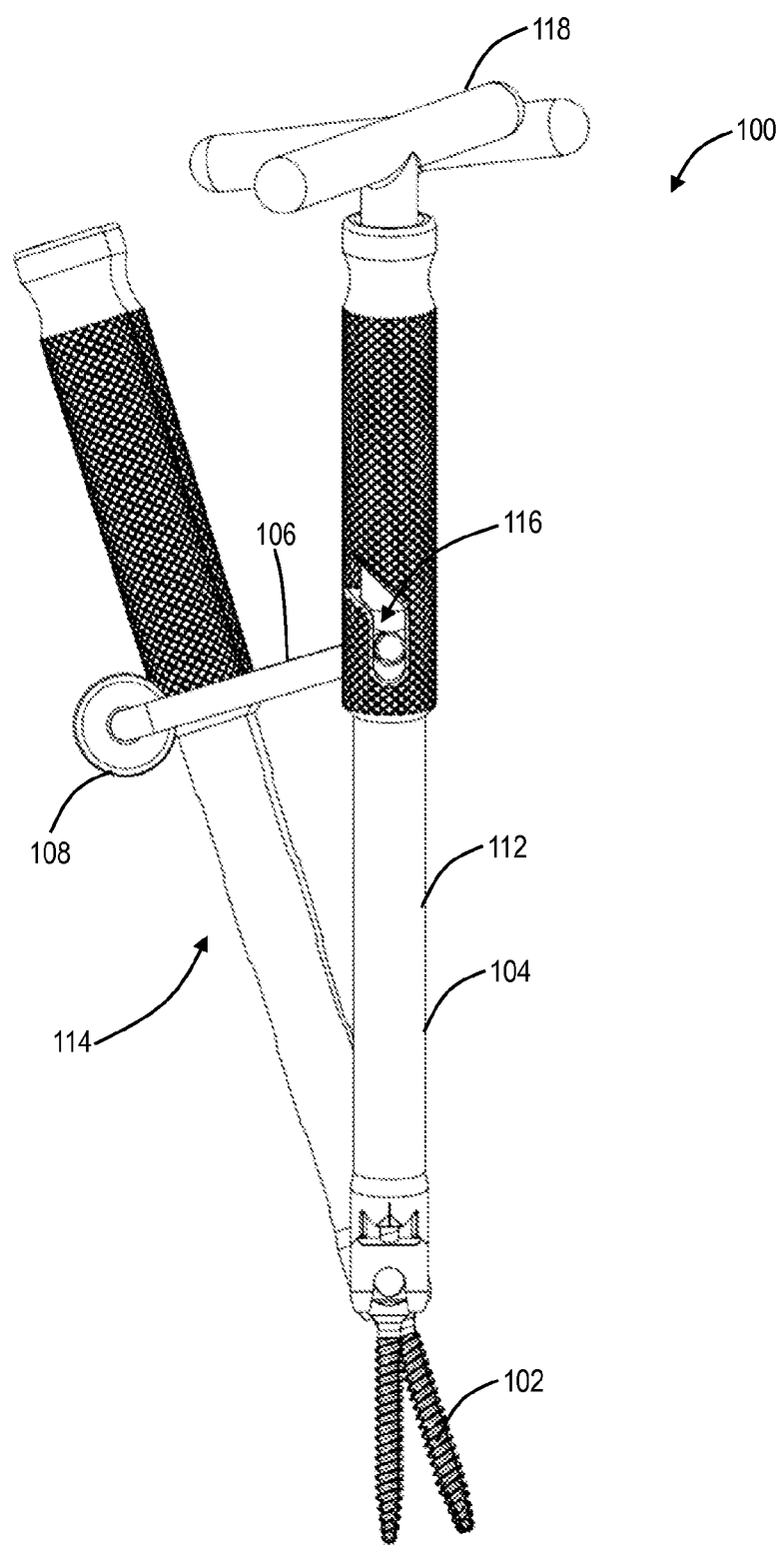
FIG. 2 is a planar end view further illustrating the spinal deformity correction system of FIG. 1.
Figure 3:
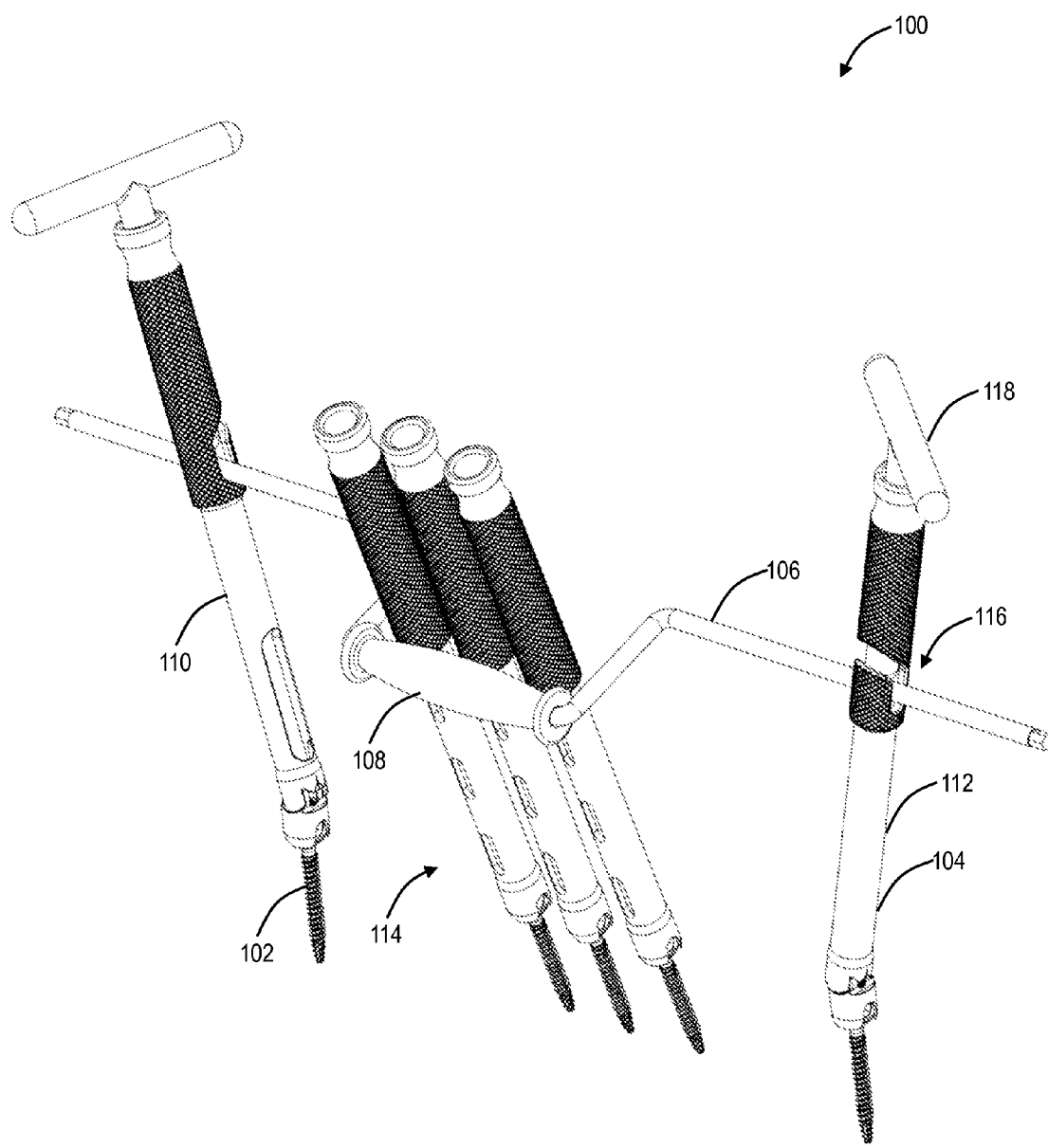
FIG. 3 is another perspective view further illustrating the spinal deformity correction system of FIG. 1.
Figure 4:
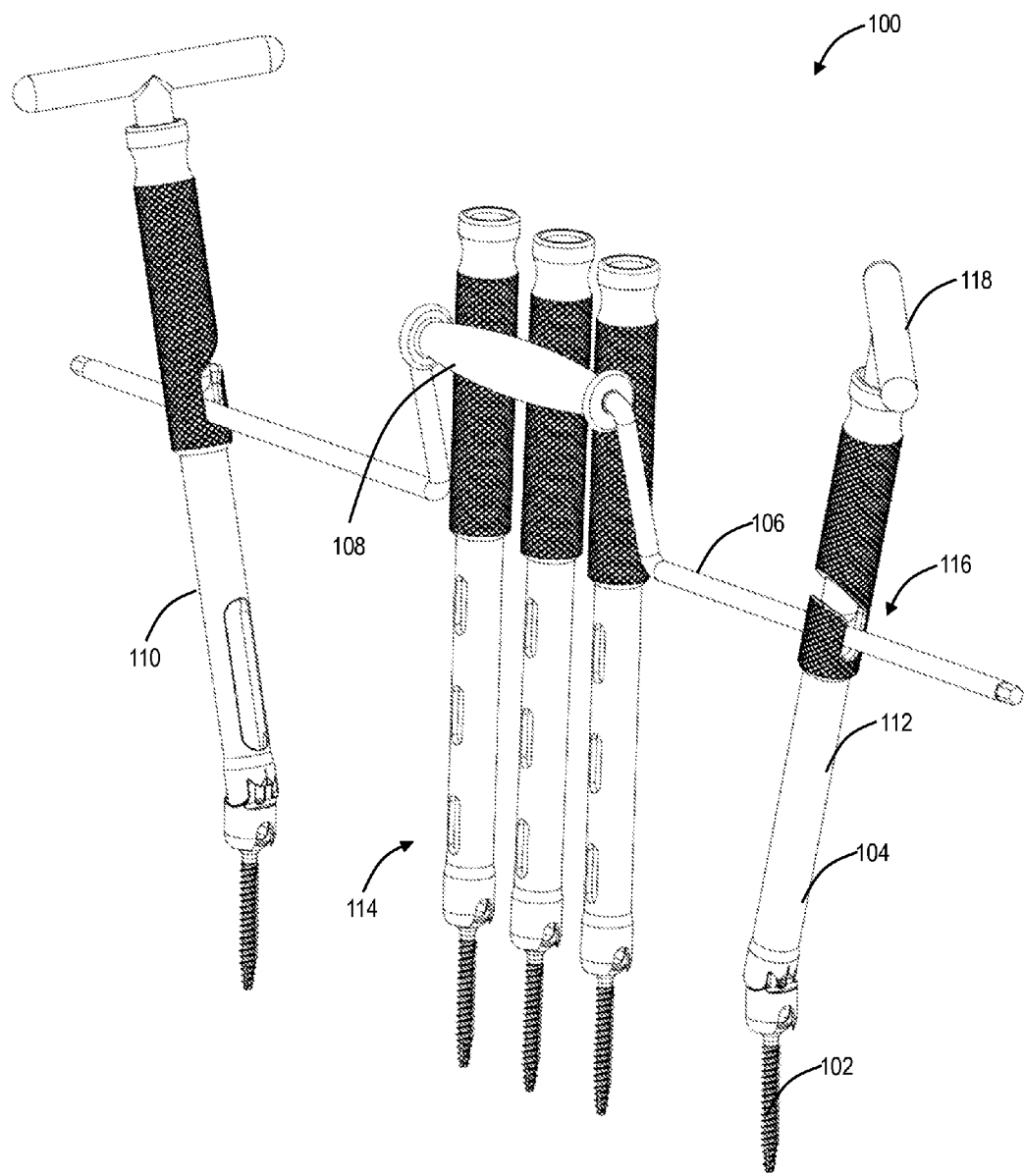
FIG. 4 is a further perspective view further illustrating the spinal deformity correction system of FIG. 1.
Figure 5:
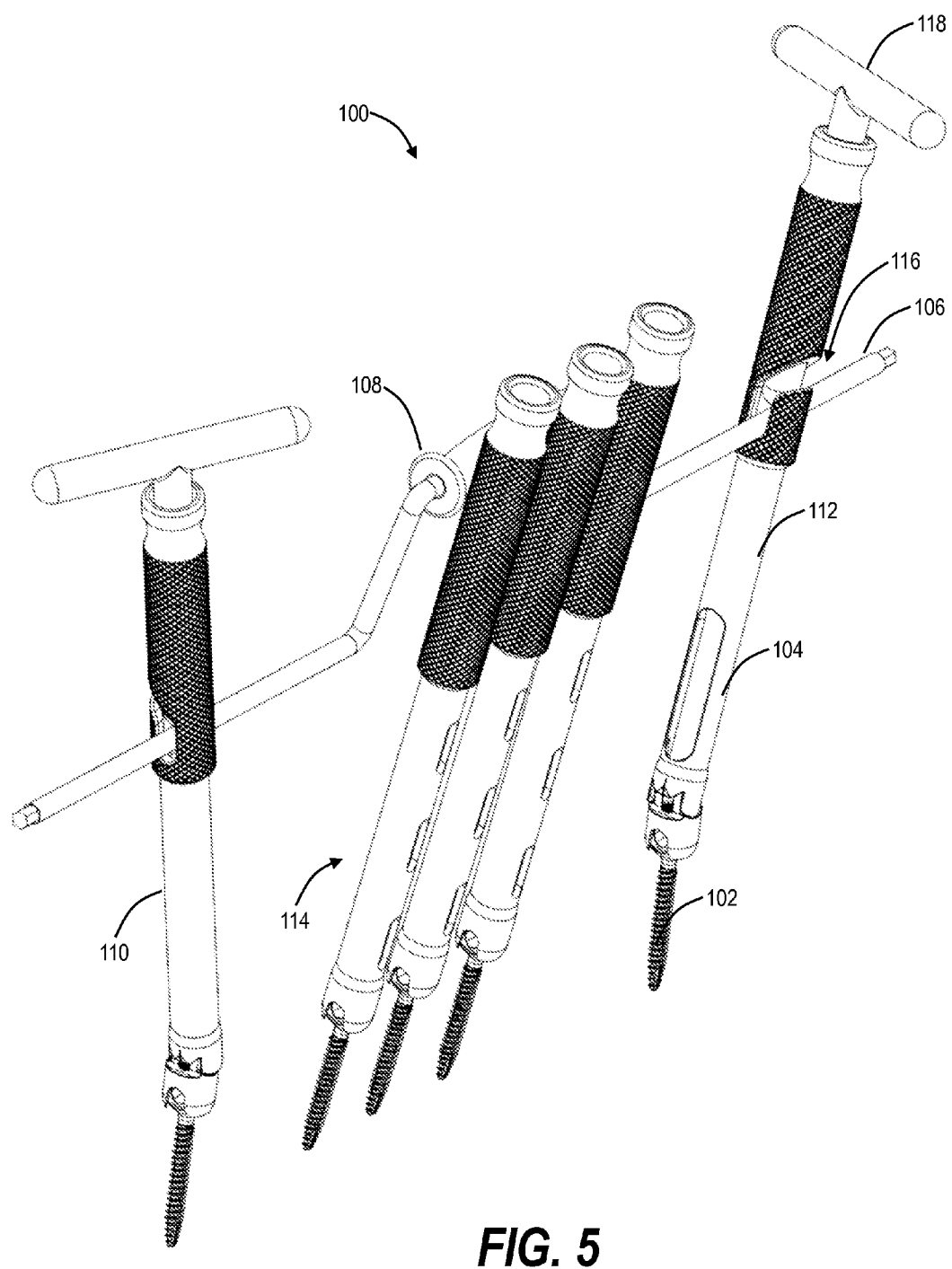
FIG. 5 is a still further perspective view further illustrating the spinal deformity correction system of FIG. 1.
Figure 6:
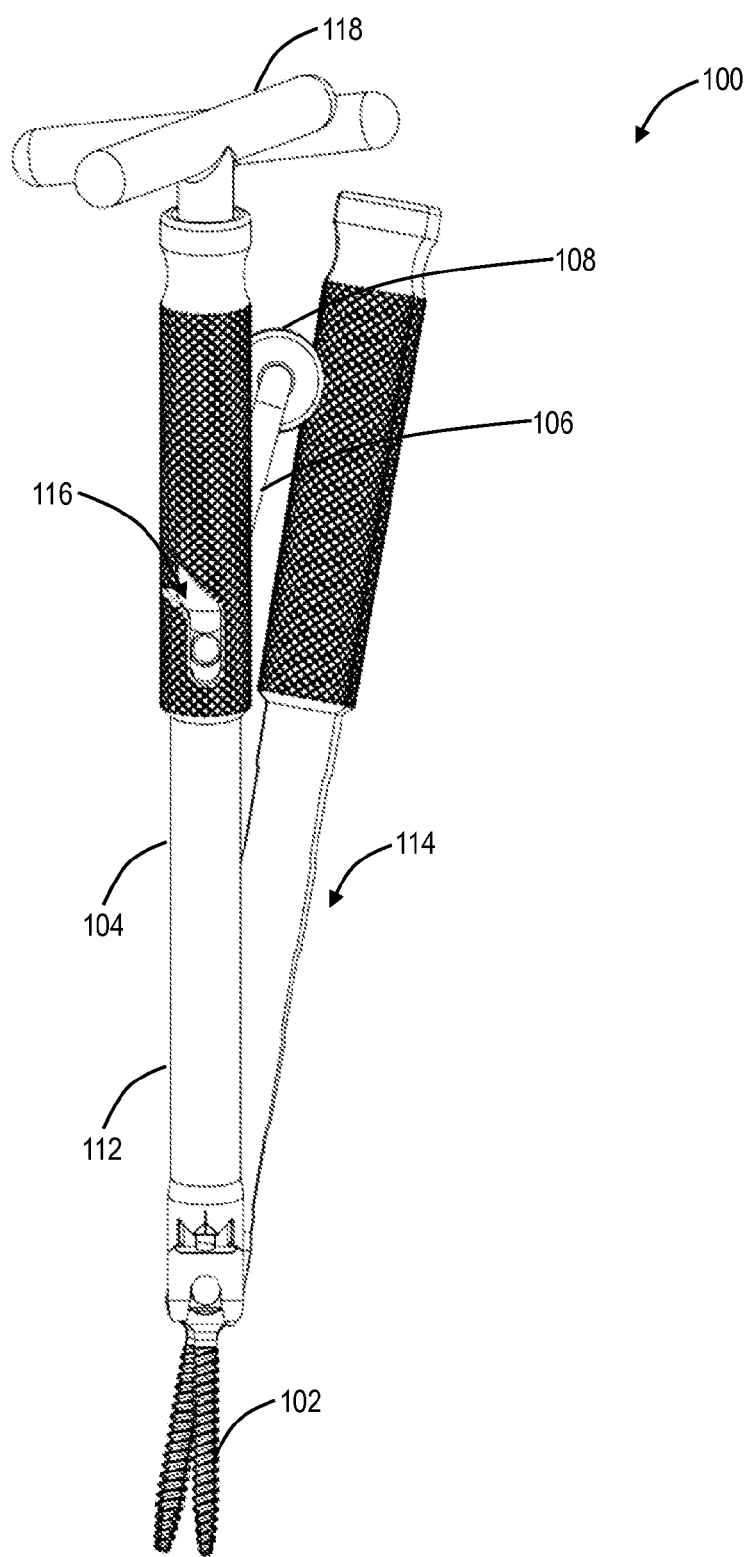
FIG. 6 is another planar end view further illustrating the spinal deformity correction system of FIG. 1.
Figure 9:
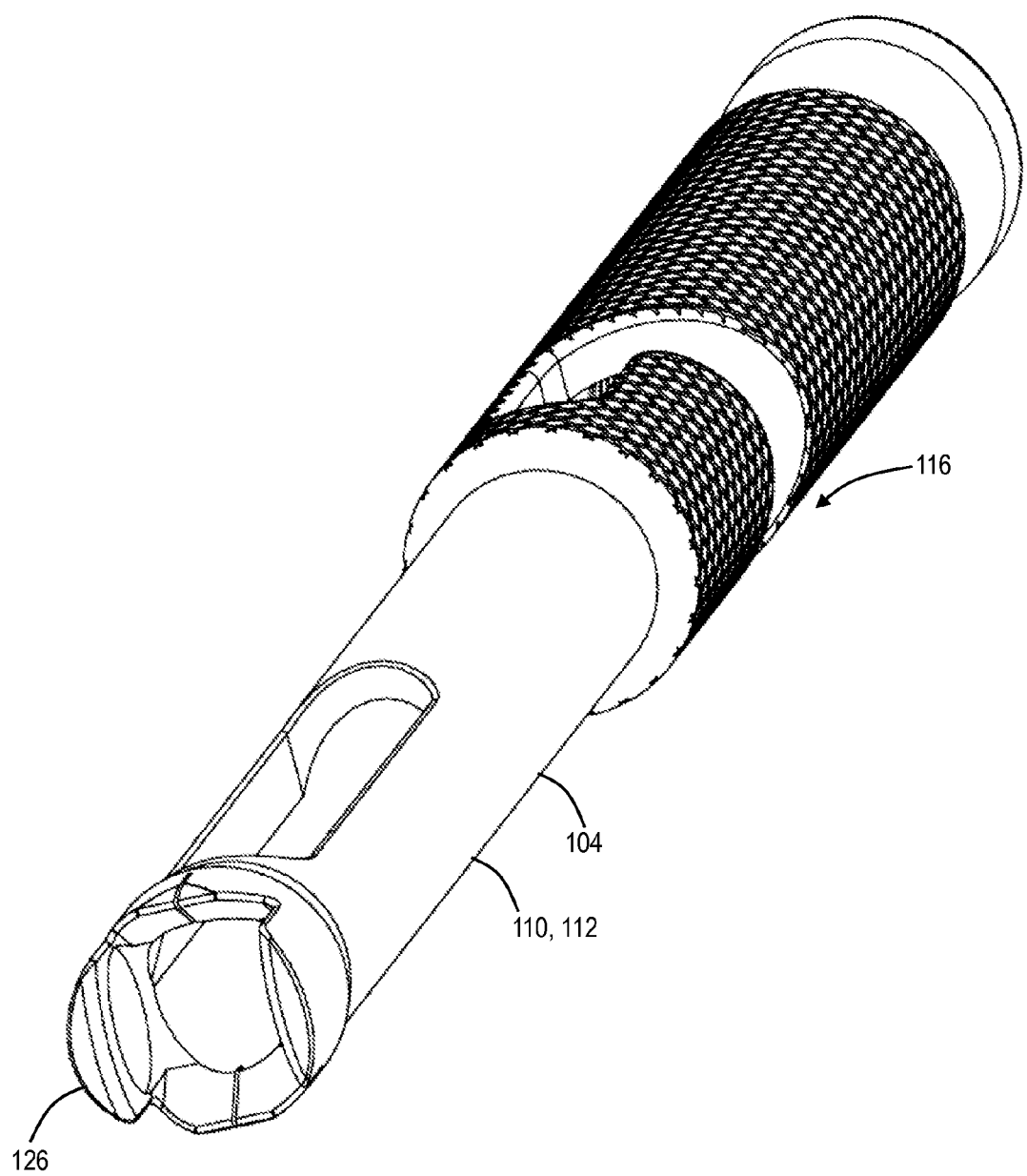
FIG. 9 is another perspective view further illustrating the cephalad/caudal extender of FIG. 7.
Figure 10:
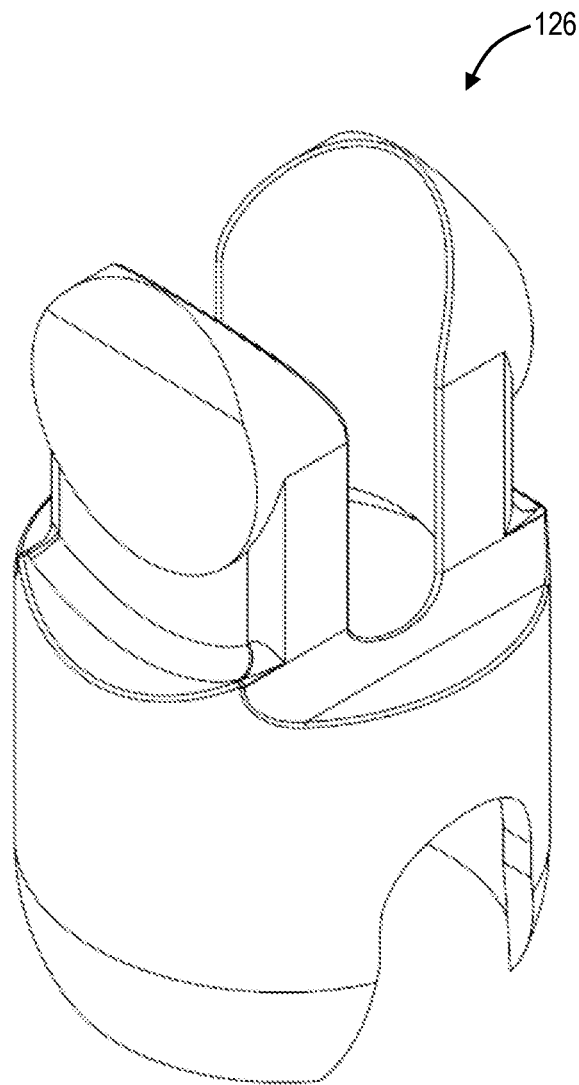
FIG. 10 is a perspective view illustrating one exemplary embodiment of a screw receiver of the spinal deformity correction system of FIG. 1.
Figures 11, 12:
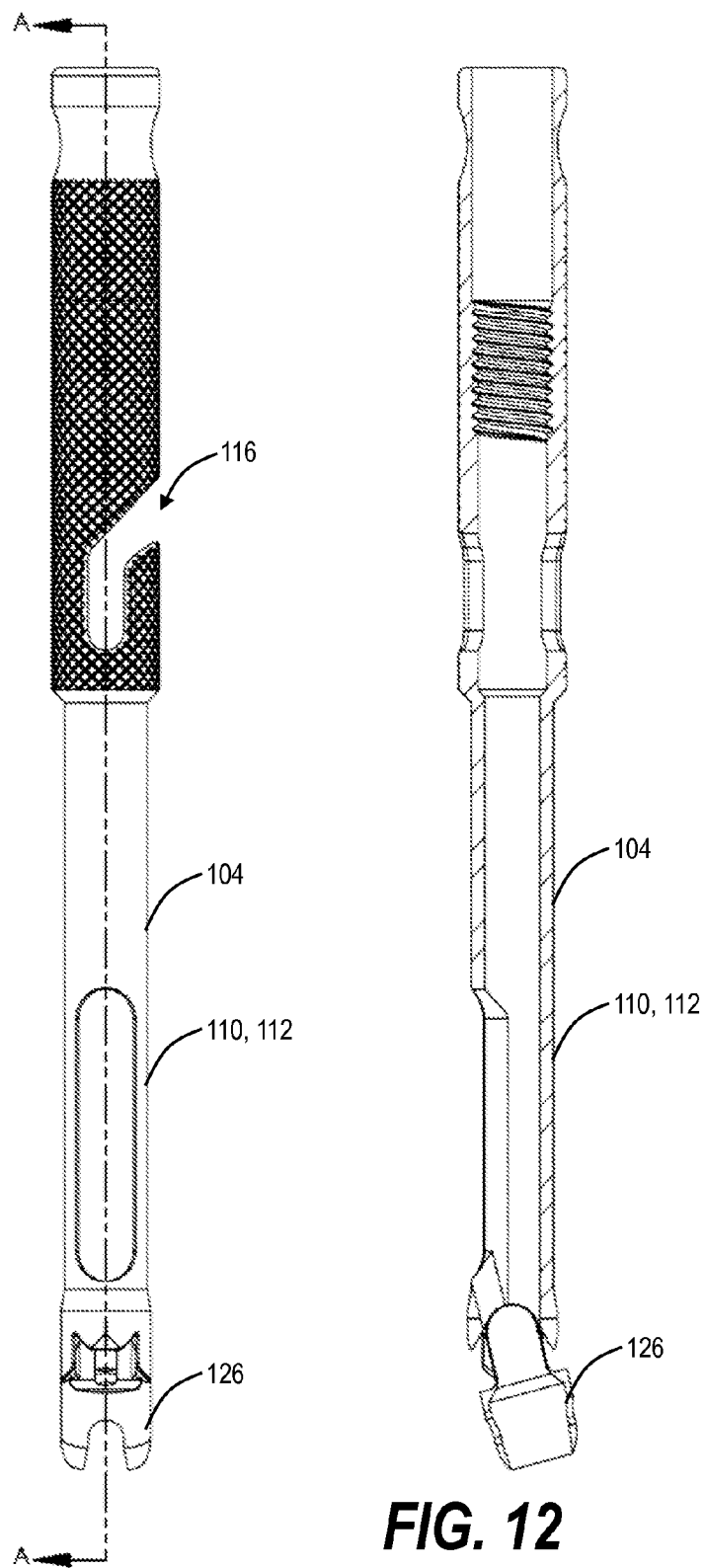
FIG. 11 is a planar side view further illustrating the cephalad/caudal extender of FIG. 7.
FIG. 12 is cross-sectional side view further illustrating the cephalad/caudal extender of FIG. 7.
Figure 13:
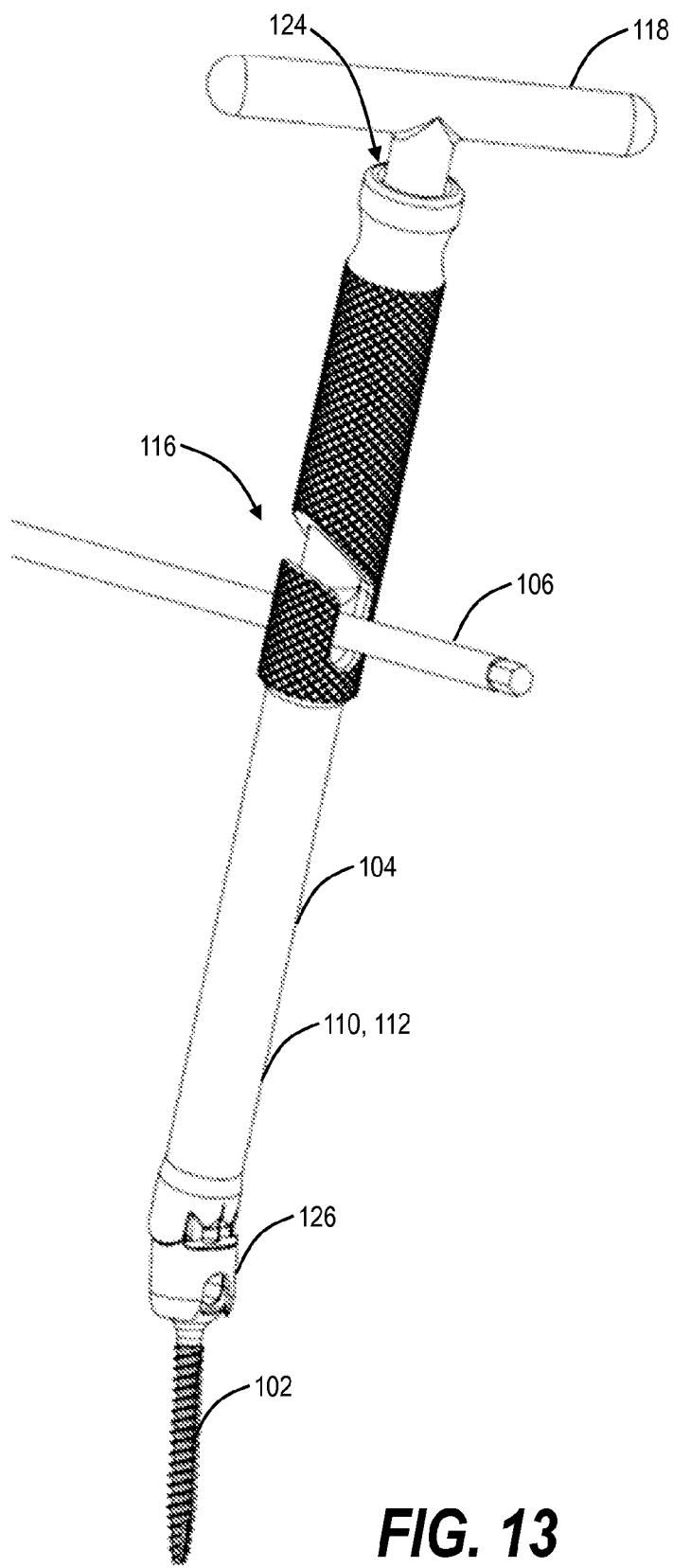
FIG. 13 is a further perspective view further illustrating the cephalad/caudal extender of FIG. 7.

FIGS. 2 and 3 illustrate the system 100 in a non-deployed configuration, before derotation has been performed. FIGS. 4-6 illustrate the system 100 in a deployed configuration, after derotation (or over-derotation) has been performed. During derotation of the intermediate vertebrae, force may be exerted by the cephalad end and the caudal end of the rotation rod 106 on the proximal ends of the cephalad extender 110 and the caudal extender 112, respectively. This force pushes the proximal ends of the cephalad extender 110 and the caudal extender 112 leftward, for example, thereby causing the cephalad vertebra and the caudal vertebra to rotate in the opposite direction, i.e. clockwise when viewed from a cranial viewpoint. Whether or not rotation of the cephalad vertebra and the caudal vertebra occurs, the result of the rotation is that the intermediate vertebrae are aligned with the cephalad vertebra and the caudal vertebra.

Alternatively, referring specifically to FIGS. 5 and 6, the intermediate vertebrae may be derotated over-center, i.e. derotated past the point at which they are aligned with the cephalad vertebra and the caudal vertebra. This over-center derotation may help to counteract the tendency of the intermediate vertebrae to rotate back to their original orientations after surgery; the degree of over-center derotation applied may depend on the rigidity of the hardware used to keep the spine in its proper shape after the surgery is complete. This hardware may be, for example, the implantable pedicle screw and rod system referenced earlier.

Notably, not all of the vertebrae of the spine to be derotated with the system 100 need be directly derotated. For example, derotation of the intermediate vertebrae relative to the cephalad vertebra and the caudal vertebra may cause intervening vertebrae to also derotate. Thus, rotational force need not be directly applied to each vertebra to be derotated.

Referring now specifically to FIGS. 7-13, in one exemplary embodiment, the cephalad extender 110 and the caudal extender 112 each include a substantially hollow shaft structure including a port 124 at the proximal end thereof; the port 124 configured to receive the locking mechanism 118 for locking the respective extender 104 to the rotation rod 106, which is coupled to the extenders 104 as described in detail herein above. In the event that a threaded locking mechanism 118 is used (see FIG. 14), the shaft structure is preferably partially internally threaded. The distal end of the cephalad extender 110 and the caudal extender 112 includes a pivotable and/or rotatable polyaxial screw receiver 126 that is hingedly and/or rotatably coupled to the shaft structure and is configured to securely receive and retain the head of the associated pedicle screw 102.

Figure 16:
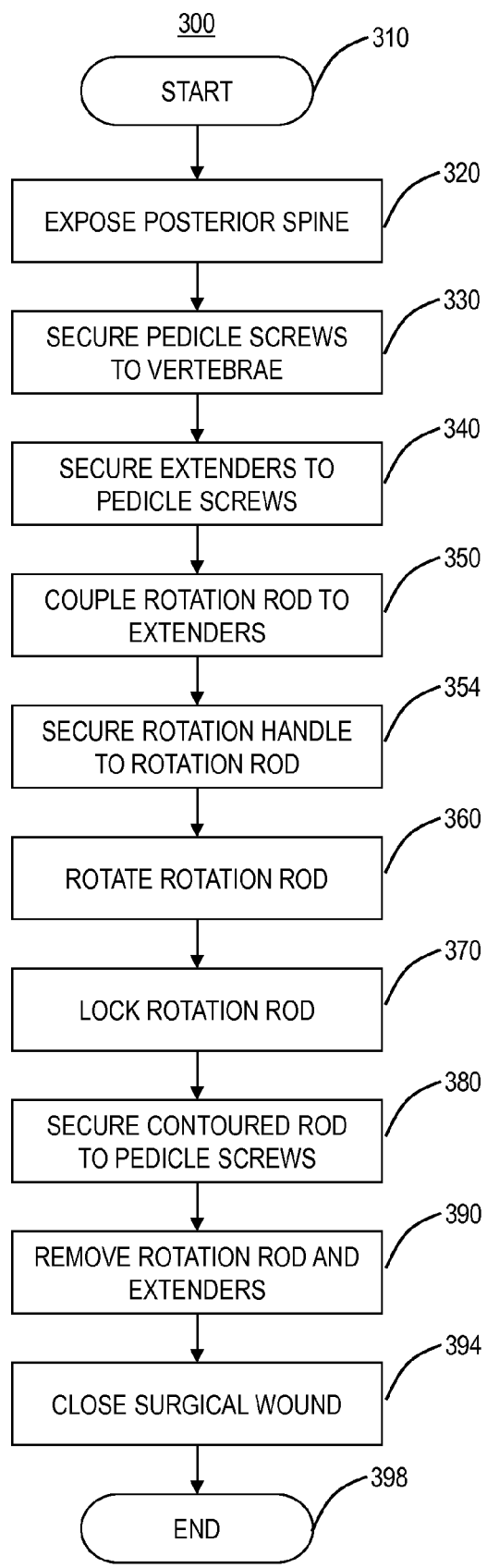
FIG. 16 is a flowchart illustrating one exemplary embodiment of a surgical method for using the spinal deformity correction system of FIG. 1.

Referring now specifically to FIG. 16, in one exemplary embodiment, a flowchart illustrates the method 300 by which the system 100 may be applied to relieve the axial rotation component of a spinal deformity. The method 300 starts 310 with a step 320 in which the posterior spine, or more specifically the treatment region of the spine, is exposed to provide access to the cephalad vertebra, the caudal vertebra, and the intermediate vertebrae. This may be accomplished via methods that are well known to those of ordinary skill in the art. A wide variety of retractors known to those of ordinary skill in the art may be used to maintain the exposure during surgery. Once the proper access has been obtained, the method 300 proceeds to a step 330 in which the pedicle screws 102 are secured to the vertebrae of the spine. This may include, but need not be limited to, the cephalad vertebra, the caudal vertebra, and the intermediate vertebrae. The pedicle screws 102 may be secured to the vertebrae through the use of methods known to those of ordinary skill in the art. Along with the pedicle screws 102, other hardware, such as couplers for receiving one or more implantable rods, may also be secured to the vertebrae of the spine.

After the pedicle screws 102 have been secured to the vertebrae, the extenders 104 may then be secured to the pedicle screws 102 in a step 340. This may be done by securing the distal ends of the extenders 104 directly to the pedicle screws 102, or alternatively, by securing the distal ends to other hardware secured to the vertebrae via the pedicle screws 102. If desired, the distal ends of the extenders 104 may have grippers, threaded connections, or other features intended to rapidly and securely secure the distal ends to the pedicle screws 102. Thus, the performance of the step 340 may entail using such features to provide the attachment. If a known type of extenders are used, the step 340 may additionally or alternatively include any known step by which such pedicle screw extenders may be secured to pedicle screws.

As mentioned previously, the system 100 may be used in conjunction with known systems for restoring proper lordosis, kyphosis, and/or lateral straightness to the spine. Such methods may, according to some embodiments, use the same pedicle screws 102 and/or extenders 104 as the method 300. Such methods may, according to certain embodiments, be carried out before the method 300 proceeds beyond the step 340 so that, when the method 300 proceeds, the spine already has the proper lordosis, kyphosis, and/or lateral straightness. Once the extenders 104 have been secured to the pedicle screws 102, the method 300 may proceed to a step 350 in which the rotation rod 106 is coupled to the extenders 104. With reference to the system 100, the performance of the step 350 may entail positioning the intermediate portion and the roller 108 of the rotation rod 106 leftward of the proximal ends of the intermediate extenders 114, for example. The performance of the step 350 may further include coupling the cephalad end of the rotation rod 106 to the coupling mechanism 116 of the cephalad extender 110, and coupling the caudal end of the rotation rod 106 to the coupling mechanism 116 of the caudal extender 112, such that the rotation rod 106 is able to rotate relative to the coupling mechanisms 116 of the cephalad extender 110 and the caudal extender 112.

After the rotation rod 106 has been rotatably coupled to the cephalad extender 110 and the caudal extender 112 and positioned, the method 300 may proceed to a step 354 in which the rotation handle is secured to the rotation rod 106. This may alternatively be done prior to performance of the step 350, or may be omitted in the event that the rotation handle is pre-attached to or formed as a single piece with the rotation rod 106, optionally as roller 108. This step may be carried out according to any of the methods set forth previously. After the rotation handle has been secured to the rotation rod 106, the method 300 may proceed to a step 360 in which the rotation rod 106 is rotated to urge derotation of the intermediate vertebrae, as described previously. This rotation of the rotation rod 106 may be accomplished, for example, by grasping the distal end of the rotation handle and then pushing and/or pulling it to urge the rotation rod 106 to rotate counterclockwise or clockwise when viewed from a cranial viewpoint. The rotation of the rotation rod 106 may cause the intermediate vertebrae to rotate, relative to the cephalad vertebra and the caudal vertebra, counterclockwise or clockwise when viewed from a cranial viewpoint, thereby rotating the spine and the system 100.

Once the rotation rod 106 has been rotated, the method 300 may proceed to a step 370 in which the rotation rod 106 is locked in its orientation relative to the cephalad extender 110, the caudal extender 112, and/or the intermediate extenders 114, thereby keeping the intermediate vertebrae in the derotated (or over-center derotated) condition until the configuration of the spine can be more permanently secured. This may be done, for example, by actuating the locking mechanisms mentioned in conjunction with the couplings mechanisms 116 of the cephalad extender 110 and the caudal extender 112. Alternatively, a separate locking mechanism may be used, or a person (such as the person that rotated the rotation handle), may exert continued and steady pressure on the rotation handle to ensure that significant additional rotation does not occur.

With the rotation rod 106 locked against further rotation, the method 300 may proceed to a step 380 in which spine is locked in the derotated (or over-center derotated) state. As mentioned previously, the system 100 may be used in conjunction with a pedicle screw and rod system, or more specifically, a rod contouring system, as known to those of ordinary skill in the art. The performance of the step 380 may entail securing the implantable rod of such a system to the pedicle screws 102. For a rod contouring system, the rod may first be contoured to match the desired lordosis and/or kyphosis of the spine. Polyaxial connectors or the like, as known to those of ordinary skill in the art, may be used to accommodate variation in the positions and/or orientations of the pedicle screws 102, as described herein above.

If desired, a single rod may be attached to all of the pedicle screws 102, such that the single rod extends from pedicle screw 102 on the cephalad vertebra to the pedicle screw 102 on the caudal vertebra. An additional implantable rod may alternatively or additionally be secured to the other side of the spine. Additionally or alternatively, an implantable rod need not extend the full length of the treatment region, but may instead extend, for example, from the intermediate vertebrae to the cephalad vertebra or from the intermediate vertebrae to the caudal vertebra. Multiple implantable rods may be used, if desired, for each of the left and right sides of the spine.

If an implantable pedicle screw and rod system is used to lock the spine in its derotated state, the same implantable system may, if desired, be used to lock in the proper lordosis, kyphosis, and/or lateral straightness of the spine. Such lordosis, kyphosis, and/or lateral straightness may have been adjusted through the use of methods known to those of ordinary skill in the art prior to performance of the step 380.

Once the spine has been locked in the derotated state, the method 300 may proceed to a step 390 in which the rotation rod 106, the rotation handle, and the extenders 104 are removed from the spine. This may be done, for example, by performing the step 354, the step 350, and the step 340 in reverse. More precisely, the rotation handle may be removed from the rotation rod 106, the rotation rod 106 may be decoupled and removed from the extenders 104, and the extenders 104 may be detached from the pedicle screws 102. Once the extenders 104, the rotation rod 106, and the rotation handle have been removed, the method 300 may proceed to a step 394 in which the surgical wound is closed. This may be carried out through the use of methods known to those of ordinary skill in the art. If an implantable pedicle screw and rod system or other implant system is used to maintain the kyphosis, lordosis, derotation, and/or lateral straightness of the spine, such a system may remain in place when the surgical wound is closed. The method 300 may then end 398.

The system 100 is only one of many systems that may be used to provide spinal derotation within the scope of the present invention. Similarly, the method 300 is only one exemplary method. Other systems and methods may be used within the scope of the present invention, as will be recognized by a person of ordinary skill in the art, with the aid of the present disclosure. For example, the system 100 may have a rotation rod 106 and a plurality of extenders 104, including an intermediate extender 114, which are configured differently from their counterparts described herein above. The intermediate extender 114 may have a distal end (not shown) similar to that of the intermediate extender 114 of the previous embodiment, and may also have a proximal end and an intermediate portion that are configured differently from those of the intermediate extender 114. More precisely, the proximal end may have an interface designed to engage the rotation rod 106 such that the rotation rod 106 is retained relative to the proximal end, but is able to rotate relative to the proximal end. The interface may have a pair of slots that are aligned with each other across the axis of the proximal end. The slots may be sized to receive the rotation rod 106. Each of the slots may terminate at a distal end that limits how far the rotation rod 106 is able move toward the corresponding distal end of the intermediate extender 114 when the rotation rod 106 is retained within the slots. The interface may also have a set screw or the like with a threaded portion (not shown) that protrudes into the interior of the proximal end through a threaded hole (not shown). Rotation of the set screw may cause the threaded portion to intrude into or retract from the interior of the proximal end.

The system 100 may also have a cephalad extender 110 and a caudal extender 112 which may be substantially identical to the intermediate extender 114. Alternatively, the cephalad extender 110 and/or the caudal extender 112 may be configured differently from the intermediate extender 114. The rotation rod 106 may have a cephalad end and a caudal end that are aligned with each other along an axis, and an intermediate portion that is offset from the axis. The shape of the intermediate portion may be similar to that of the intermediate portion of the previous embodiment, or may be shaped differently. The intermediate portion may have no roller like the roller 108 of the previous embodiment, but may rather be designed to engage the interface of the proximal end of each intermediate extender 114, for example, by fitting within the slots of each interface, as indicated previously. The system 100 may include additional components that help rotatably retain and fixedly retain the cephalad and caudal ends of the rotation rod 106. Such components may take a wide variety of forms.

A rotation yoke or the like, two of which may optionally be included in the system 100 (one for the cephalad extender 110 and one for the caudal extender 112), may be used. The rotation yokes may be used to couple the cephalad and caudal ends of the rotation rod 106 to the interfaces of the cephalad and caudal extenders 110 and 112 of the system 100. As mentioned previously, the cephalad and caudal extenders 110 and 112 may be identical to the intermediate extender 114. Thus, the cephalad and caudal extenders 110 and 112 may each have an interface with slots. Each rotation yoke may have a head and a shank that extends from the head. The shank may have a slot with a proximal end that has a generally hemi-cylindrical shape. The rotation yoke may be inserted into the proximal end such that the shank passes into the interior of the proximal end and the head rests against the proximal surface of the proximal end. The slot may be aligned with the slots of the interface of the proximal end so that, as the shank is pushed distally, the slot receives the corresponding cephalad or caudal end of the rotation rod 106. The shank may have a length selected such that, when the head abuts the proximal surface of the proximal end, the cephalad or caudal end of the rotation rod 106 rests on or near the proximal end of the slot and the distal end of the slots of the interface. The proximal end may be relatively smooth so as to permit rotation of the rotation rod 106 against the proximal end. Thus, the proximal end and the distal end may cooperate to define a cradle that permits the corresponding cephalad or distal end of the rotation rod 106 to rotate within the cradle, while restricting or preventing any translation of the cephalad or distal end apart from motion along the axis defined by the cephalad and caudal ends of the rotation rod 106. Accordingly, each head may operate in conjunction with the corresponding cephalad or caudal extender 110 or 112 to define a revolute joint for the corresponding cephalad or caudal end of the rotation rod 106. After insertion, the set screw may be used to secure the head in its proper operating position relative to the interface. On or two locking yokes may also be used with the system 100 (one for the cephalad extender 110 and/or one for the caudal extender 112). The locking yoke may have a configuration similar to that of the rotation yoke, and may thus have a head and a shank with a slot. The slot may have a proximal end different from the proximal end of the slot of the rotation yoke in that the proximal end may be ridged, knurled, or otherwise shaped to provide resistance to rotation of the rotation rod 106 against the proximal end. The proximal end may, if desired, have flats, teeth, or other locking features that interface with optional corresponding features on the cephalad end or the caudal end of the rotation rod 106. Thus, the proximal end may provide resistance to rotation of the rotation rod through frictional engagement and/or mechanical locking. If desired, two locking yokes may be used, one for the cephalad extender 110 and one for the caudal extender 112. Alternatively, only a single locking yoke may be used, and may only be applied to the cephalad extender 110 or the caudal extender 112.

A method similar to the method 300 may be used to provide spinal derotation with the aid of these alternative systems 100. The system 100 may be used, initially, with the step 320, the step 330, and the step 340 as described. The method 300 may optionally be adapted for use with the system 100 through the use of methods that will be shown and described in connection with FIGS. 17 and 18, as follows.

Figure 17:
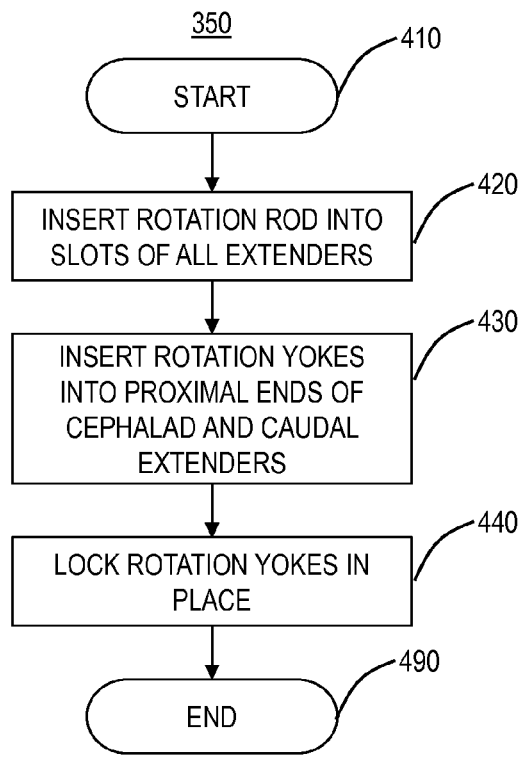
FIG. 17 is a flowchart illustrating a sub-method associated with the surgical method of FIG. 16.
Figure 18:
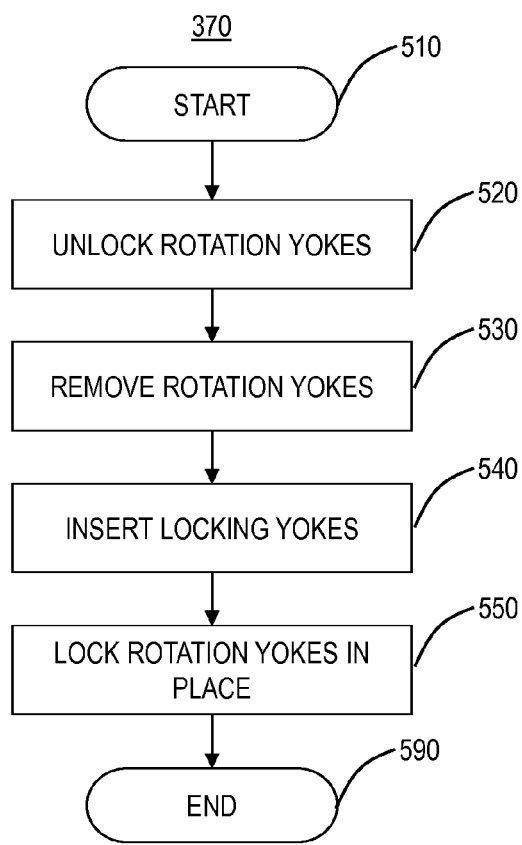
FIG. 18 is another flowchart illustrating a further sub-method associated with the surgical method of FIG. 16.

Referring now specifically to FIG. 17, a flowchart illustrates the step 350 of the method 300, as applied to the alternative system 100. The step 350 may include the coupling of the rotation rod 106 to the cephalad and caudal extenders 110 and 112 of the system. The step 350 may start 410 with a step 420 in which the cephalad and caudal ends of the rotation rod 106 are inserted into the slots of the interfaces of the cephalad and caudal extenders 110 and 112. Then, in a step 430, the rotation yokes may be inserted into the proximal ends of the cephalad and caudal extenders 110 and 112. After the rotation yokes have been fully inserted into the proximal ends, the rotation yokes may be locked in place within the proximal ends in a step 440. This may be done, for example, by rotating the set screws of the cephalad and caudal extenders 110 and 112, such that the threaded portion of each set screw is driven into the corresponding proximal end. The threaded portion may then abut the shank of the rotation yoke and may push against the shank to restrict or prevent withdrawal of the shank from the proximal end. After the rotation yokes have been locked in place, the step 350 may then end 490. Rotation of the rotation rod 106 may then be carried out, with the aid of the rotation yokes, to derotate the spine, in the step 360. Once the rotation rod 106 has been rotated to the desired orientation, the step 370 may be carried out.

Referring to FIG. 8, a flowchart illustrates the step 370 of the method 300, as applied to the alternative system 100. The step 370 may include locking the rotation rod 106 against further rotation, through the use of one or two locking yokes. The step 370 may start 510 with a step 520 in which one or both of the rotation yokes are unlocked, for example, by loosening the set screw to withdraw the threaded portion of the set screw from engagement with the shank of each rotation yoke. Then, in a step 530, one or both rotation yokes may be removed from the proximal end of the cephalad and/or caudal extenders 110 and/or 112. After one or both of the rotation yokes have been removed from the corresponding proximal ends, in a step 540, a locking yoke may be inserted into each proximal end from which a rotation yoke was removed. As with insertion of the rotation yokes into the proximal end, each locking yoke may be inserted until the proximal end of the slot rests against the corresponding cephalad or caudal end of the rotation rod 106, thereby trapping the cephalad or caudal end between the proximal end and the distal end of each of the slots of the interface. Abutment of the proximal end against the cephalad or caudal end of the rotation rod 106 may restrict or prevent further rotation of the rotation rod 106. After each locking yoke has been fully inserted into the corresponding proximal end, each locking yoke may be locked in place within the proximal end in a step 550. This may be done, for example, by rotating the set screw of the cephalad and/or caudal extenders 110 and/or 112, such that the threaded portion of each set screw is driven into the corresponding proximal end. The threaded portion may then abut the shank of the locking yoke and may push against the shank to restrict or prevent withdrawal of the shank from the proximal end. After each locking yoke has been locked in place, the step 370 may then end 990. After completion of the step 370, the step 380, the step 390, and the step 394 may be applied to the system as set forth in the description. The system 100 may advantageously help to provide for simpler and more predictable engagement and/or locking of the rotation rod 106 relative to the cephalad and/or caudal extenders 110 and/or 112.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A system for the correction of a spinal deformity by derotating one or more vertebrae of the spine, comprising:
    a rotation rod;
    a cephalad extender configured to be selectively rotatably coupled to the rotation rod and coupled to a cephalad vertebra of the spine;
    a caudal extender configured to be selectively rotatably coupled to the rotation rod and coupled to a caudal vertebra of the spine; and
    one or more intermediate extenders configured to be selectively coupled to one or more intermediate vertebrae of the spine;
    wherein, when the rotation rod is selectively rotated, a portion of the rotation rod engages a portion of the one or more intermediate extenders, causing the one or more intermediate extenders to rotate about an axis of the spine, thereby causing the one or more intermediate vertebrae to rotate about the axis of the spine; and wherein one or more of the cephalad extender and the caudal extender comprise a locking mechanism for selectively preventing relative rotation with the rotation rod.

2. The system of claim 1, further comprising a rotation handle configured to be selectively coupled to the rotation rod.

3. The system of claim 1, wherein the rotation rod comprises an off-axis portion that engages the portion of the one or more intermediate extenders.

4. The system of claim 3, wherein the rotation rod further comprises a roller disposed about the off-axis portion that engages the portion of the one or more intermediate extenders.

5. The system of claim 1, wherein the cephalad extender, the caudal extender, and the one or more intermediate extenders each comprise a screw configured to engage a respective vertebra.

6. The system of claim 5, wherein one or more of the cephalad extender and the caudal extender comprise an end portion that is one or more of pivotable and rotatable and that selectively retains a head of the respective screw.

7. The system of claim 1, further comprising a coupling mechanism for rotatably coupling the one or more intermediate extenders to the rotation rod.

8. The system of claim 1, further comprising a screw and rod system configured to secure the spine in a derotated state after the one or more intermediate vertebrae are rotated about the axis of the spine.

* * * * *